United States Patent [19]

Raulfs et al.

[11] Patent Number: 5,071,987
[45] Date of Patent: Dec. 10, 1991

[54] QUINOLINE-4-CARBOXYLIC ACID DERIVATIVES

[75] Inventors: Friedrich-Wilhelm Raulfs, Mannheim; Udo Mayer, Frankenthal, both of Fed. Rep. of Germany

[73] Assignee: BASF Aktiengesellschaft, Ludwigshafen, Fed. Rep. of Germany

[21] Appl. No.: 474,327

[22] Filed: Feb. 2, 1990

[30] Foreign Application Priority Data

Feb. 22, 1989 [DE] Fed. Rep. of Germany ....... 3905339

[51] Int. Cl.$^5$ .......................................... C07D 215/50
[52] U.S. Cl. .................................. 546/168; 546/101; 546/169; 546/173
[58] Field of Search ........................ 546/108, 169, 101

[56] References Cited

U.S. PATENT DOCUMENTS

| | | | |
|---|---|---|---|
| 3,985,376 | 10/1976 | Bauman et al. | 282/27.5 |
| 4,625,027 | 11/1986 | Zink et al. | 544/62 X |
| 4,668,966 | 5/1987 | Zink et al. | 544/74 X |
| 4,680,299 | 7/1987 | Hesson | 514/311 |

FOREIGN PATENT DOCUMENTS

| | | |
|---|---|---|
| 0256180 | 2/1988 | European Pat. Off. |
| 462136 | 7/1928 | Fed. Rep. of Germany ...... 546/168 |
| 2029591 | 3/1980 | United Kingdom . |
| 2136823 | 9/1984 | United Kingdom . |
| 2162652 | 2/1986 | United Kingdom . |

OTHER PUBLICATIONS

J. Prakt. Chem., vol. 38, pp. 582–584, W. Pfitzinger, "Chinolinderivate Aus Isatinsaure".

Dyes and Pigments, vol. 8, 1987, pp. 281–290, D. W. Rangnekar et al., "Synthesis of 2-Aryl-6-Substituted Quinolines and Their Use as Fluorescent Brightening Agents".

Chem. Ber., 20, pp. 277–281, O. Doebner, "Ueber Alpha-Alkyl-Cinchoninsauren", 1887.

Primary Examiner—David B. Springer
Attorney, Agent, or Firm—Oblon, Spivak, McClelland, Maier & Neustadt

[57] ABSTRACT

Quinoline-4-carboxylic acids derivatives are useful as dye-forming components for pressure- and heat-sensitive recording materials and have of the general formula I

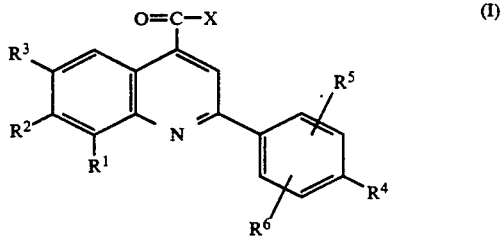

where one of
$R^1$, $R^2$ and $R^3$ is hydrogen while the other two are each independently of each other hydrogen, fluorine, chlorine, bromine, linear or branched $C_1$–$C_5$-alkyl, hydroxyl, $C_1$–$C_{10}$-alkoxy, which may be interrupted in the alkyl by 1 or 2 oxygen atoms, or is

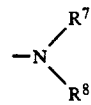

$R^7$ is hydrogen, methyl or ethyl and
$R^8$ is $C_1$–$C_4$-alkanoyl, benzoyl, p-chlorobenzoyl, $C_1$–$C_6$-alkyl, benzyl or p-chlorobenzyl, or
$R^1$ and $R^2$ together are a fused-on benzene ring,
$R^2$ and $R^3$ together are unsubstituted or $C_1$–$C_4$-alkyl-substituted methylenedioxy or ethylenedioxy,
$R^4$ is hydroxyl, $C_1$–$C_{10}$-alkoxy, which may be interrupted by 1–4 oxygen atoms, or unsubstituted or chlorine-substituted phenyl-$C_1$–$C_2$-alkoxy,
$R^5$ is hydroxyl or $C_1$–$C_{10}$-alkoxy, although ortho-disposed $R^4$ and $R^5$ together may also be methylenedioxy or 1,2-ethylenedioxy,
$R^6$ is hydrogen, hydroxyl, methoxy, ethoxy, chlorine, fluorine or $C_1$–$C_4$-alkyl, and
X $C_1$–$C_{20}$-alkoxy, benzyloxy, p-chlorobenzyloxy, phenylethyloxy, cyclopentoxy, cyclohexoxy or

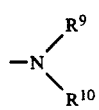

where
$R^9$ is hydrogen, methyl or ethyl and
$R^{10}$ is hydrogen, $C_1$–$C_{20}$-alkyl, unsubstituted or chlorine- or methoxy- or methyl-monosubstituted or -disubstituted phenyl or a radical of the formula

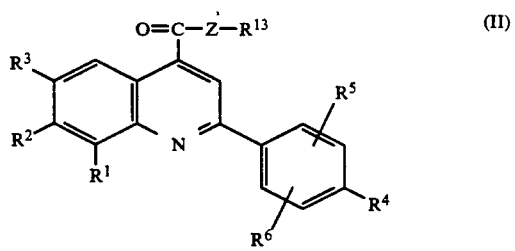

where
$R^1$ to $R^6$ are each as defined above,
Z is oxygen or $>$N-$R^9$ and
$R^{13}$ is linear or branched $C_2$–$C_{10}$-alkylene, which may be interrupted by up to 4 oxygen atoms, or is 1,2-, 1,3- or 1,4-xylylene.

8 Claims, No Drawings

QUINOLINE-4-CARBOXYLIC ACID DERIVATIVES

The prior art discloses recording materials containing dye-forming components that produce yellow to orange colorings. For instance, DE-A-2 227 597 describes pyridine compounds that produce yellow to orange colorings on paper coated with electron acceptors. EP-A-109 930 and EP-A-159 295 disclose bisquinazoline compounds which are suitable for use as dye-forming components for pressure- or heat-sensitive recording materials. Furthermore, EP-A-256 180 and GB-A-2 136 823 disclose dye-forming components based on dihydroxystyrylquinoline.

The prior art dye-forming components have insufficient light fastness not only in the neutral but also in the protonated state.

It is an object of the present invention to provide dye-forming components that produce yellow to orange colorings and are improved in light fastness We have found that this object is achieved by the quinoline-4-carboxylic acid derivatives according to the present invention.

The present invention accordingly provides quinolinecarboxylic acid derivatives of the formula I

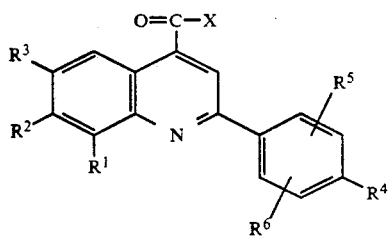

where one of
$R^1$, $R^2$ and $R^3$ is hydrogen while the other two are each independently of each other hydrogen, fluorine, chlorine, bromine, linear or branched $C_1$-$C_5$-alkyl, hydroxyl, $C_1$-$C_{10}$-alkoxy, which may be interrupted in the alkyl by 1 or 2 oxygen atoms, or is

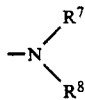

$R^7$ is hydrogen, methyl or ethyl and
$R^8$ is $C_1$-$C_4$-alkanoyl, benzoyl, p-chlorobenzoyl, $C_1$-$C_6$-alkyl, benzyl or p-chlorobenzyl, or
$R^1$ and $R^2$ together are a fused-on benzene ring,
$R^2$ and $R^3$ together are unsubstituted or $C_1$-$C_4$-alkyl-substituted methylenedioxy or ethylenedioxy,
$R^4$ is hydroxyl, $C_1$-$C_{10}$-alkoxy, which may be interrupted by 1-4 oxygen atoms, or unsubstituted or chlorine-substituted phenyl-$C_1$-$C_2$-alkoxy,
$R^5$ is hydroxyl or $C_1$-$C_{10}$-alkoxy, although ortho-disposed $R^4$ and $R^5$ together may also be methylenedioxy or 1,2-ethylenedioxy,
$R^6$ is hydrogen, hydroxyl, methoxy, ethoxy, chlorine, fluorine or $C_1$-$C_4$-alkyl, and
X $C_1$-$C_{20}$-alkoxy, benzyloxy, p-chlorobenzyloxy, phenylethyloxy, cyclopentoxy, cyclohexoxy or

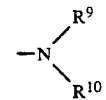

where
$R^9$ hydrogen, methyl or ethyl and
$R^{10}$ is hydrogen, $C_1$-$C_{20}$-alkyl, unsubstituted or chlorine- or methoxy- or methyl-monosubstituted or -disubstituted phenyl or a radical of the formula

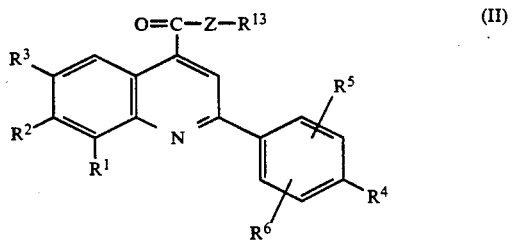

where
$R^1$ to $R^6$ are each as defined above,
Z is oxygen or $>N-R^9$ and
$R^{13}$ is linear or branched $C_2$-$C_{10}$-alkylene, which may be interrupted by up to 4 oxygen atoms, or is 1,2-, 1,3- or 1,4-xylylene.

The quinoline-4-carboxylic acid derivatives of the present invention produce together with electron acceptors as used in customary CF coats intense yellow to orange colorings which, compared with colorings obtained with the dye-forming components as described in EP-A-109 930, GB-A-2 136 823 and DE-A-2 227 597, are superior in light fastness.

Besides hydrogen, fluorine, chlorine, bromine or hydroxyl, $R^1$, $R^2$ and $R^3$ may each also be:
a) linear or branched $C_1$-$C_5$-alkyl, e.g. methyl, ethyl, propyl, isopropyl, butyl, isobutyl, tert-butyl, pentyl or isoamyl;
b) $C_1$-$C_{10}$-alkoxy which may be interrupted in the alkyl by 1 or 2 oxygen atoms, such as methoxy, ethoxy, propoxy, isopropoxy, butoxy, isobutoxy, tert-butoxy, pentoxy, hexoxy, 2-ethylhexoxy or 2-(ethoxy)ethoxy;
c) a radical of the formula

e.g. acetylamino, propionylamino, benzoylamino, acetylmethylamino, N,N-dimethylamino, N,N-diethylamino, N-methyl-N-butylamino or N-ethyl-N-hexylamino. One of $R^1$, $R^2$ and $R^3$ must be hydrogen.

$R^1$ and $R^2$ together may also be a fused-on benzene ring.

Preferably, $R^1$ and $R^3$ are each hydrogen and $R^2$ is hydrogen, methyl or methoxy.

It is also preferable for $R^2$ and $R^3$ together to be unsubstituted or methyl-substituted methylene dioxy or ethylenedioxy.

Hydroxyl aside, $R^4$ is $C_1$-$C_{10}$-alkoxy, which may be interrupted by 1,2,3, or 4 oxygen atoms, or unsubstituted or chlorine-substituted phenyl-$C_1$-$C_2$-alkoxy. Specific examples are: methoxy, ethoxy, propoxy, isopropoxy, butoxy, isobutoxy, tert-butoxy, pentoxy, hexoxy, 2-ethylhexoxy, octyloxy, decyloxy, 2-(ethoxy)ethoxy, 2-(propoxy)ethoxy and 2'-ethoxy-2-ethoxyetheneoxy, benzyloxy, p-chlorobenzyloxy and phenylethyloxy.

$R^5$, besides hydroxyl, is $C_1-C_{10}$-alkoxy such as methoxy, ethoxy, propoxy, isopropoxy, butoxy, isobutoxy, tert-butoxy, pentoxy, hexoxy, 2-ethylhexoxy or octyloxy.

$R^6$, besides having the abovementioned specific meanings, can be for example methyl, ethyl, propyl, isopropyl, butyl or isobutyl.

If $R^4$ together with $R^5$ is methylenedioxy or 1,2-ethylenedioxy, the radicals

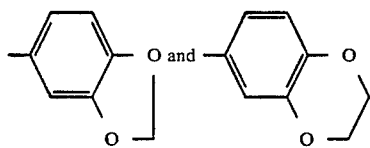

may be singled out.

Examples of preferred combinations of substituents $R^4$, $R^5$ and $R^6$ are summarized in Table 1.

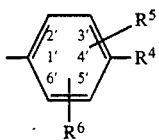

TABLE 1

| $R^4$ | $R^5$ | $R^6$ |
|---|---|---|
| —OCH₃ | 2'-OCH₃ | H |
| —OCH₃ | 3'-OCH₃ | H |
| —OCH₃ | 3'-OCH₃ | 5'-OCH₃ |
| —OC₂H₅ | 2'-OC₂H₅ | H |
| —OH | 3'-OCH₃ | H |
| —OH | 3'-OCH₃ | 5'-Cl |
| —OCH₃ | 5'-OCH₃ | 2'-CH₃ |
| —OCH₃ | 5'-OCH₃ | 2'-C₂H₅ |
| —OCH₃ | 3'-OCH₃ | 2'-OCH₃ |
| —OCH₃ | 2'-OH | —OCH₃ |
| —OCH₃ | 3'-OCH₃ | 5'-CH(CH₃)₂ |
| —OCH₃ | 2'-OCH₃ | 5'-OCH₃ |
| —OC₂H₅ | 3'-OCH₃ | H |
| —OC₃H₇ | 3'-OCH₃ | H |
| —OC₄H₉ | 3'-OCH₃ | H |
| —OC₄H₉ | 2'-OC₄H₉ | H |

Particular preference is given to dye-forming components I where $R^5$ is in the 2'- or 3'-position and $R^6$ is hydrogen.

Besides having the specific meanings aforementioned above,

X is $C_1-C_{20}$-alkoxy such as methoxy, ethoxy, propoxy, isopropoxy, butoxy, isobutoxy, sec-butoxy, tert-butoxy, pentoxy, isoamyloxy, tert-amyloxy, aneoipentyloxy, hexyloxy, 2-ethylhexyloxy, heptoxy, octyloxy, nonyloxy, decyloxy, dodecyloxy, cetyloxy or octanedecyloxy, or a radical of the formula

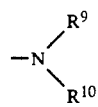

$R^9$ is hydrogen, methyl or ethyl. $R^{10}$ besides hydrogen is:

i) $C_1-C_{20}$-alkyl such as methyl, ethyl, propyl, isopropyl, butyl, isobutyl, sec-butyl, tert-butyl, hexyl, 2-ethylhexyl, octyl or decyl;

ii) substituted or unsubstituted phenyl such as phenyl, 4-chlorophenyl, 4-methoxyphenyl, 4-methylphenyl, 2-methylphenyl, 3-methylphenyl, or 3,4-dimethylphenyl, or iii) a radical of the formula II.

If X is a radical of the formula II, Z can be oxygen or $>N-R^9$. A bridge member $R^{13}$, besides having the specific meanings mentioned above, can be linear or branched $C_2-C_{10}$-alkylene which may be interrupted by up to 4 oxygen atoms. Specific examples are:

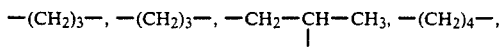

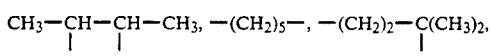

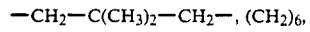

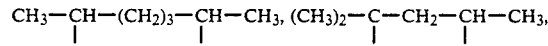

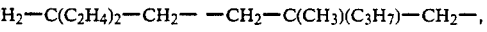

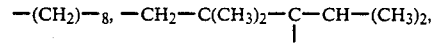

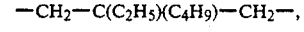

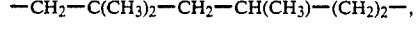

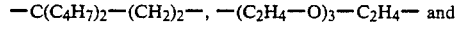

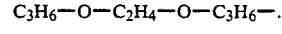

The quinoline compounds (I) according to the present invention are colorless or slightly yellowish compounds whose solutions in inert organic solvents such as partially hydrogenated bi- or terphenyl, alkylbenzenes, alkylnaphthalenes, alkylated dibenzylbenzenes, paraffin oil or mineral oil produce on contact with electron acceptors, such as carboxylic, sulfonic or mineral acids, kaolin, bentonite, activated acid clay, aluminum silicate, attapulgite or acidic organic polymers, for example, condensation products of formaldehyde and phenols or phenolsulfonic acids, yellow to orange colorings. Owing to these properties, these compounds can be microencapsulated. On application of pressure, contact with electron acceptors leads to a dye or color being formed at the point of the application of pressure.

Suitable microencapsulation techniques are known for example from U.S. Pat. Nos. 2 800 457, 2 800 458, DE-A-2 119 933 and EP-A-26 914. The compounds according to the invention can also be finely divided in wax or oil/wax mixtures by the method described in U.S. Pat. No. 3 103 404. Paper coated therewith releases the dye on the application of pressure and a color is produced on a sheet of paper coated on the front with electron acceptors.

Similarly, the quinoline-4-carboxylic acid derivatives may be used for example as described in DE-A-2 228 581 or DE-A-2 110 854 as dye-forming components in heat-sensitive recording materials or for example in copying systems as described in GB-A-2 029 591 or GB-A-2 162 652.

The light fastness of the resulting colorings is better with the quinoline-4-carboxylic acid compounds (I) than that of the colorings obtained with the compounds of the above-cited prior art.

Quinoline-4-carboxylic acids that are required for synthesizing compounds of the formula I can be prepared by the method of W. Pfitzinger (J. Prakt. Chem. 38 (1988), 582) whereby an isatin of the general formula (III)

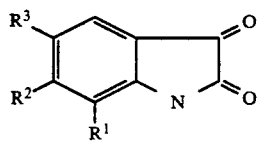

is reacted with an acetophenone of the formula (IV)

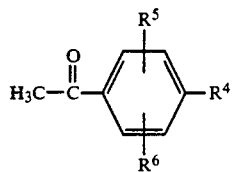

for example in a strong alcoholic alkali metal hydroxide solution, preferably potassium hydroxide in ethanol. This reaction can also be carried out for example by phase transfer catalysis as described in Dyes and Pigments 8 (1987), 281–290.

The quinoline-4-carboxylic acids obtained are then esterified or amidated to (I) in a conventional manner.

A further method for preparing quinoline-4-carboxylic acids is described in Chem. Ber. 20 (1987), 277. There an aniline of the formula (V)

$$R^3 \text{—} \overset{R^2}{\underset{R^1}{\bigcirc}} \text{—} NH_2 \quad (V)$$

and an aldehyde of the formula (VI)

$$R^5 \text{—} \overset{R^4}{\underset{R^6}{\bigcirc}} \text{—} CHO \quad (VI)$$

are reacted with pyruvic acid in a $C_1$–$C_5$-alkanol, preferably in methanol or ethanol, under reflux. The quinoline carboxylic acids formed are then esterified or amidated to (I) in a conventional manner.

The Examples which follow further illustrate the invention. The percentages are by weight.

EXAMPLE 1

44 g of pyruvic acid were added dropwise to 75.5 g of vanillin and 46 g of aniline in 500 ml of ethanol at 0°–5° C. Two hours' stirring at room temperature down to room temperature, 42.4 g of 2-(4,-hydroxy-3'-methoxyphenyl)quinoline-4-carboxylic acid came down as a precipitate.

14.7 g of this carboxylic acid were taken up in 64 g of methanol. Hydrogen chloride gas were passed in at the reflux temperature for 1½ hours. After cooling down, concentrated ammonia solution was added to adjust the pH to 8.5, and the precipitated crystals were filtered off with suction and recrystallized from methanol. 9.8 g were obtained of methyl 2-(4'-hydroxy-3'-methoxyphenyl)quinoline-4-carboxylate having a melting point of 144° C. In toluene the $\lambda_{max}$ is 363 nm and in a 2% strength solution of hydrochloric acid in methanol it is 420 nm.

The method of Example 1 was also used to prepare the compounds indicated in the table below.

TABLE 2

| Example No. | Compound | $\lambda_{max}$ [nm] neutral | $\lambda_{max}$ [nm] acid | Melting point [°C.] |
|---|---|---|---|---|
| 2 | (structure: methyl 2-(3',4'-dimethoxyphenyl)quinoline-4-carboxylate) | 366 | 412 | 105–109 |

TABLE 2-continued

| Example No. | Compound | $\lambda_{max}$ [nm] neutral | [nm] acid | Melting point [°C.] |
| --- | --- | --- | --- | --- |
| 3 | ![structure 3] | 359 | 392 | 93–96 |
| 4 | ![structure 4] | 363 | 408 | 133–136 |
| 5 | ![structure 5] | 356 | 408 | 126–128 |
| 6 | ![structure 6] | 367 | 416 | 115, 5 |

EXAMPLE 7

44 g of pyruvic acid were added dropwise in 82.5 g of veratrumaldehyde and 46 g of aniline in 500 ml of ethanol with ice-cooling. This is followed by 2 hours at room temperature and 4 hours under reflux. After cooling, 48.7 g of 2-(3',4'-dimethoxyphenyl)quinoline-4-carboxylic acid were isolated.

EXAMPLE 8

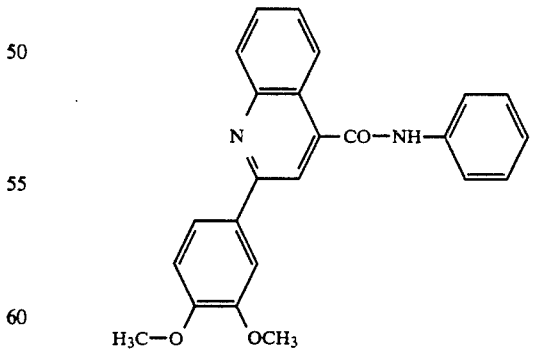

7.72 g of the 2-(3',4'-dimethoxyphenyl)quinoline-4-carboxylic acid prepared as described in Example 7 were added to 40 g of thionyl chloride. The mixture was stirred until a deep red solution had formed. The excess thionyl chloride was then distilled off under reduced pressure at a bath temperature of 40° C. The residue was introduced into 60 g of aniline at 25°-30° C. and briefly heated to 80° C. After cooling, the mixture was diluted with 250 ml of methanol, and the crystals were filtered off, washed with water and dried. Yield: 8.72 g of 2-(3',4'-dimethoxyphenyl)quinoline-4-carboxyanilide, melting point: 235°-237° C., $\lambda_{max}$ in toluene 354 nm and in 2% strength methanolic hydrochloric acid 398 nm.

The method of Example 8 was also used to prepare the compounds of Examples 9 to 12 with the corresponding alcohols being used in the case of Examples 11 and 12. In this case, after the esterification had ended, the mixture was made slightly alkaline with concentrated ammonia solution.

pressure at a bath temperature of 40° C. Half the acid chloride was added to 40 g of ethylene glycol a little at a time. The mixture was heated to 70° C. for 1 hour. It was then discharged into 200 ml of water, and the suspension was made slightly alkaline with ammonia solution. The ester formed was extracted with toluene. The organic phase was separated off and dried by distilling off the toluene-water azeotrope. 4 g of pyridine and the other half of the acid chloride were added to the dried organic phase, and the mixture was heated at 75° C. for 1 hour. The resulting salt of the diester was filtered off with suction, washed with toluene and dried. The salt was introduced into dilute ammonia solution by stirring Filtration, washing and drying gave 8.8 g of glycol bis(2-(3',4'-dimethoxyphenyl)quinoline-4-carboxylate). Melting point 182°-184° C., $\lambda_{max}$ in toluene 368 nm; $\lambda_{max}$ in 2% strength methanolic hydrochloric acid 416 nm.

The compounds of Examples 14 to 21 were likewise prepared by the method of Example 13.

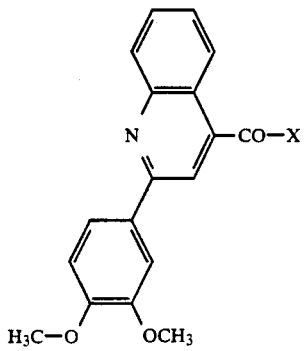

| Example No. | X | $\lambda_{max}$ neutral | [nm] acid | Melting point [°C.] |
|---|---|---|---|---|
| 9 | —NH—CH₂—CH(CH₃)₂ | 350 | 398 | 180, 5 |
| 10 | —NH—CH₂—CH(C₂H₅)—(CH₂)₃—CH₃ | 351 | 398 | 145–147 |
| 11 | —O(CH₂)₂—C₆H₅ | 366 | 412 | 103–106 |
| 12 | —O(CH₂)₃—CH₃ | 365 | 411 | 84–86 |

EXAMPLE 13

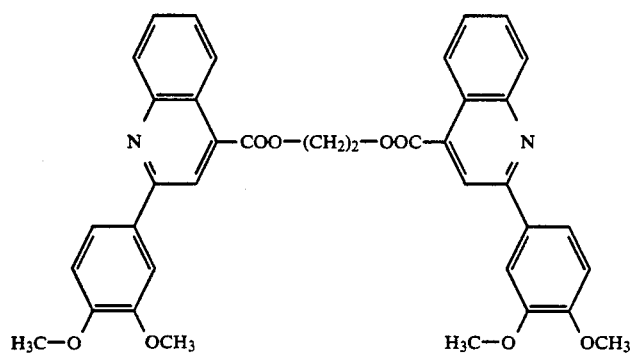

15.44 g of the 2-(3',4'-dimethoxyphenyl)quinoline-carboxylic acid of Example 7 were introduced into 80 g of thionyl chloride. After the reaction had ended, the excess thionyl chloride was distilled off under reduced

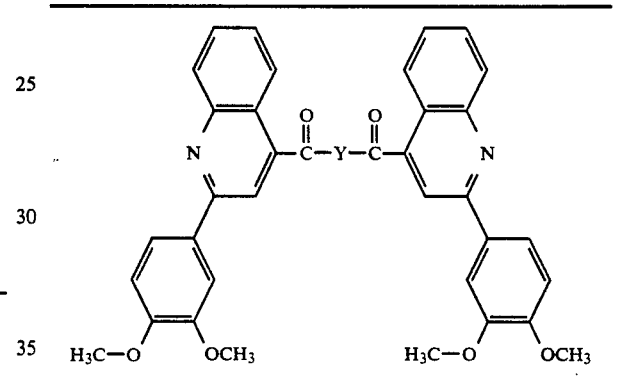

| Example No. | Y | $\lambda_{max}$ neutral | [nm] acid | Melting point [°C.] |
|---|---|---|---|---|
| 14 | —O(CH₂)₆O— | 366 | 413 | 150 |
| 15 | —O—H₂C—C(C₂H₅)₂—CH₂—O— | 368 | 417 | 141 |
| 16 | —O(CH₂)₄O— | 367 | 414 | 151–156 |
| 17 | —O(CH₂)₃O— | 368 | 416 | |
| 18 | —(O(CH₂)₂)₄O— | 366 | 413 | 105–109 |
| 19 | —O—CH(CH₃)(CH₂)₂CH(CH₃)—O— | 366 | 413 | 166–171 |

-continued

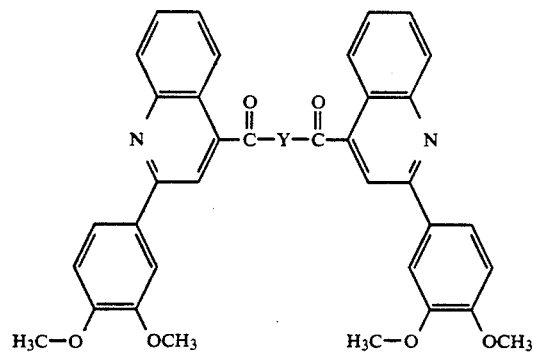

| Example No. | Y | $\lambda_{max}$ [nm] neutral | [nm] acid | Melting point [°C.] |
|---|---|---|---|---|
| 20 | —N—CH₂—C(CH₃)(CH₃)—CH₂—N— (H, H) | 354 | 399 | 220–223 |
| 21 | —N(CH₂)₃N— (H, H) | 355 | 400 | 191–196 |

The starting 2-(3′,4′-dimethoxyphenyl)quinoline-4-carboxylic acids required were prepared by the method of Example 7. The ethyl esters were prepared from the acid chlorides. To this end, the particular acid was reacted with excess thionyl chloride. The excess thionyl chloride was distilled off under reduced pressure, and the residue was admixed with ethanol, added dropwise with cooling. The hydrochlorides of the particular ethyl quinoline-4-carboxylates were made slightly alkaline with concentrated ammonia solution and the ethyl 2-(3′,4′-dimethoxyphenyl)quinoline-4-carboxylates were isolated.

| Example No. | Quinoline-4-carboxylic ester | $\lambda_{max}$ [nm] neutral | [nm] acid | Melting point [°C.] |
|---|---|---|---|---|
| 22 | 6-methoxy-2-(3',4'-dimethoxyphenyl)quinoline-4-carboxylic acid ethyl ester | 383 | 425 | 105 |
| 23 | benzo-fused 2-(3',4'-dimethoxyphenyl)quinoline-4-carboxylic acid ethyl ester | 384 | 427 | 106–110 |
| 24 | 8-methoxy-2-(3',4'-dimethoxyphenyl)quinoline-4-carboxylic acid ethyl ester | 364 | 405 | 128–131 |
| 25 | 8-hydroxy-2-(3',4'-dimethoxyphenyl)quinoline-4-carboxylic acid ethyl ester | 368 | 404 | 88 |

| Example No. | Quinoline-4-carboxylic ester | λ_max [nm] neutral | [nm] acid | Melting point [°C.] |
|---|---|---|---|---|
| 26 | 7-methoxy, 4-COOC₂H₅, 2-(3,4-dimethoxyphenyl)quinoline | 371 | 419 | 114 |
| 27 | 6-isopropyl, 4-COOC₂H₅, 2-(3,4-dimethoxyphenyl)quinoline | 369 | 412 | 101 |
| 28 | 6,7-dimethyl, 4-COOC₂H₅, 2-(3,4-dimethoxyphenyl)quinoline | 368 | 410 | 110–112 |
| 29 | 6-methyl-7-methoxy, 4-COOC₂H₅, 2-(3,4-dimethoxyphenyl)quinoline | 371 | 417 | 136–138 |
| 30 | 6-methyl-8-hydroxy, 4-COOC₂H₅, 2-(3,4-dimethoxyphenyl)quinoline | 361 | 407 | 144–150 |
| 31 | 6,8-dimethoxy, 4-COOC₂H₅, 2-(3,4-dimethoxyphenyl)quinoline | 391 | 420 | 127–129 |

Aniline was dissolved in ethanol and reacted with an aldehyde ACHO as described in Example 7 to give the corresponding quinoline-4-carboxylic acid. The esterification was carried out in the alcohols H-X indicated in the table at 80° C. while hydrogen chloride gas was passed in. Neutralization with concentrated ammonia solution and a conventional workup gave the quinoline-4-carboxylic esters indicated in the table below.

| Ex. No. | A | Quinoline-4-carboxylic ester | neutral | acid | Melting point [°C.] |
|---|---|---|---|---|---|

-continued
| Ex. No. | A | H-X | Quinoline-4-carboxylic ester | λ_max [nm] neutral | [nm] acid | Melting point [°C.] |
|---|---|---|---|---|---|---|
| 32 | 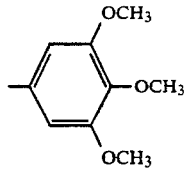 | Phenyl-ethanol | 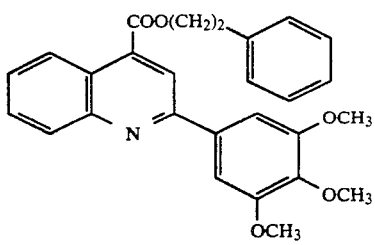 | 359 | 393 | 98–101 |
| 33 | 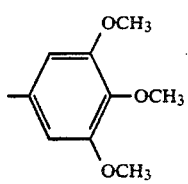 | Butanol | 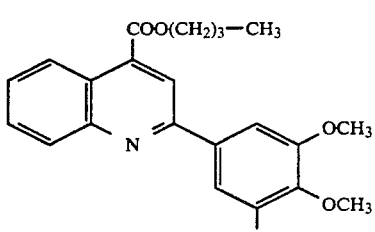 | 358 | 393 | 84–86 |
| 34 | 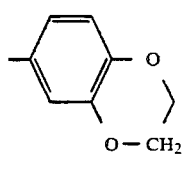 | Butanol | 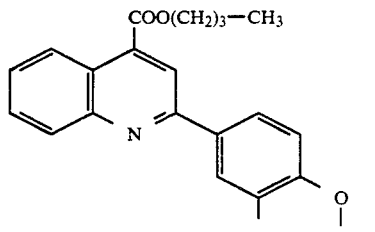 | 362 | 407 | 75 |
| 35 | 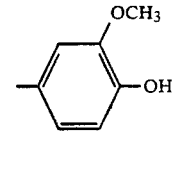 | Butanol | 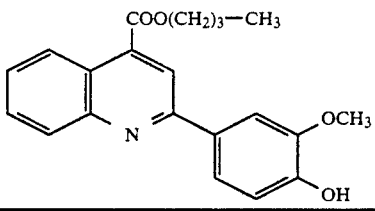 | 363 | 418 | 84 |
| Ex. No. | A | H-X | Quinoline-4-carboxylic ester | λ_max [nm] neutral | [nm] acid | Melting point [°C.] |
|---|---|---|---|---|---|---|
| 36 | 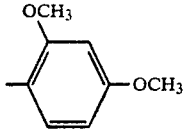 | Butanol | 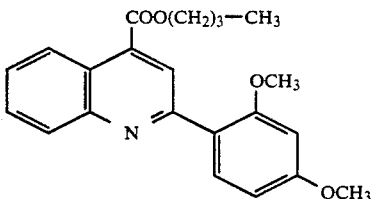 | 356 | 407 | 45 |
| 37 | 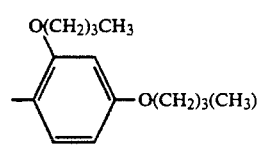 | Ethanol | 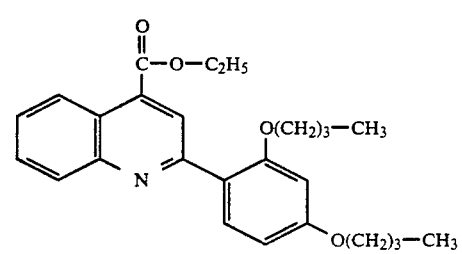 | 359 | 413 | 67 |

EXAMPLE 38

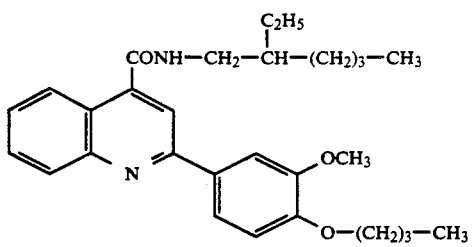

10.5 g of 2-(4'-butyoxy-3'-methoxyphenyl)quinoline-4-carboxylic acid (prepared as described in Example 7) were dissolved in 50 g of thionyl chloride, and the solution was refluxed for half an hour. The excess thionyl chloride was distilled off under reduced pressure, and the residue was introduced into 50 g of 2-ethylhexylamine with ice-water cooling. The mixture was stirred at 25° C. for 1 hour and at 80° C. for a further half hour. After cooling, 200 ml of methanol were added to dilute the mixture, and the precipitated product was washed with methanol and water and dried at 60° C. in a drying cabinet. 6.5 g were obtained of N-(2'-ethylhexyl)-2-(4'-butoxy-3'-methoxyphenyl)quinoline-4-carboxamide.

The colorless crystals melt at 118° C. and have a $\lambda_{max}$ in toluene at 352 nm. In 2% strength methanolic hydrochloric acid the $\lambda_{max}$ is 403 nm.

EXAMPLE 39

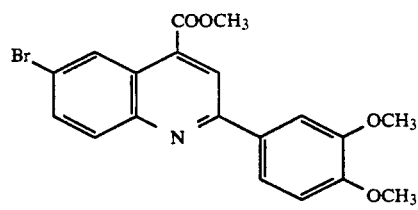

7.68 g of 5-bromoisatin, 5.41 g of 3,4-dimethoxyacetophenone, 2 g of tetrabutylammonium hydrogen sulfate and 45 g of 33% strength potassium hydroxide solution were stirred under reflux for 10 hours. The precipitated potassium salt was filtered off and suspended in water, and the suspension was brought to pH 4.5 with 10% strength hydrochloric acid. Yield: 9.22 g of 6-bromo-2-(3'4'-dimethoxyphenyl)quinoline-4-carboxylic acid. The esterification was carried out as in Example 1. 6.8 g were obtained of methyl 6-bromo-2-(3',4'-dimethoxyphenyl)quinoline-4-carboxylate. The substance has a melting point of 154° C. and a $\lambda_{max}$ in toluene of 377 nm and in 2% strength methanolic hydrochloric acid of 425 nm.

The method of Example 39 was also used to prepare the methyl quinoline-4-carboxylates indicated in the table below.

| Example No. | Methyl quinoline-4-carboxylate | $\lambda_{max}$ neutral | [nm] acid |
|---|---|---|---|
| 40 | ![structure] | 385 | 435 |
| 41 | ![structure] | 366 | 421 |
| 42 | ![structure] | 363 | 419 |

7-Methoxy-2-(2',4'-dimethoxyphenyl)quinoline-4-carboxylic acid was prepared by the method of Example 7. The acid was esterified as described in Examples 32 to 37. Amidations were carried out as described in Example 38.

| Example No. | Compound | Melting point [°C.] |
|---|---|---|
| 43 | 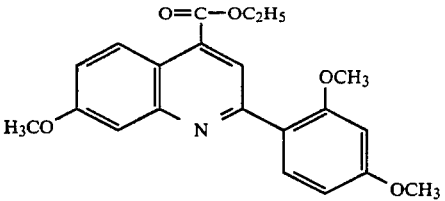 | 97-98 |
| 44 | 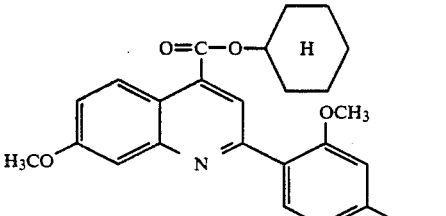 | 83-84 |
| 45 | 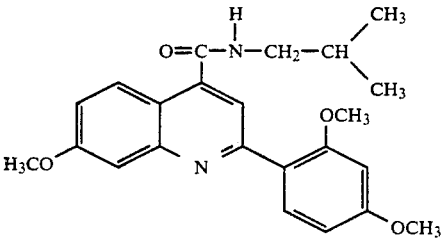 | 129-130 |
| 46 | 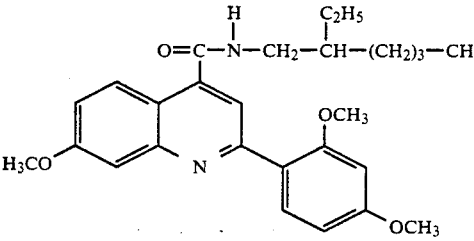 | 104,5-105,5 |
| 47 | 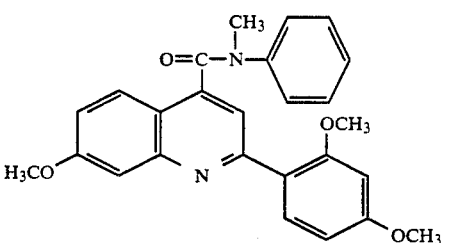 | 185-186 |
The method of Example 7 can also be used to prepare the compounds of Examples 48-52.
| Example No. | Compound | $\lambda_{max}$ neutral [nm] | acid |
|---|---|---|---|
| 48 | 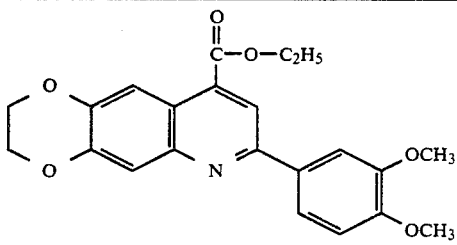 | 373 | 433 |

-continued

| Example No. | Compound | $\lambda_{max}$ neutral | [nm] acid |
|---|---|---|---|
| 49 | (structure: 6,7-ethylenedioxy quinoline-4-COOCH₃, 2-(2',4'-di-O(CH₂)₃CH₃ phenyl)) | 369 | 424 |
| 50 | (structure: 6,7-ethylenedioxy quinoline-4-COOCH₃, 2-(3',4'-dimethoxyphenyl)) | 373 | 433 |
| 51 | (structure: 6,7-methylenedioxy quinoline-4-COOCH₃, 2-(3',4'-dimethoxyphenyl)) | 370 | 432 |
| 52 | (structure: 6,7-(isopropylidenedioxy) quinoline-4-COOCH₃, 2-(3',4'-dimethoxyphenyl)) | 371 | 434 |

EXAMPLE 53

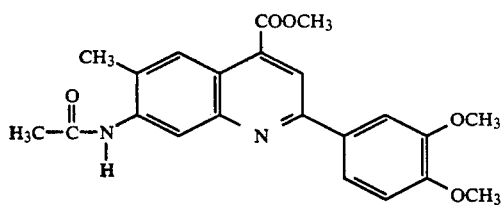

11.4 g (0.03 mol) of 2-(3',4'-dimethoxyphenyl)-6-methyl-7-acetylamino-quinoline-4-carboxylic acid prepared as described in Example 7 were added to a solution of 3.8 g (0.03 mol) of oxalyl chloride in 60 ml of toluene at room temperature under nitrogen, followed by 6.1 g (0.06 mol) of triethylamine in 30 ml of toluene with ice-water cooling. After 1.5 hours at 65°–70° C. a further 3.86 g (0.03 mol) of oxalyl chloride were added, followed 3 hours later by a further 2 g (0.02 mol). The reaction mixture was then heated at 75°–80° C. for 2.5 hours, cooled down, and admixed with 30 g of methanol and 10.1 g (0.01 mol) of triethylamine. The precipitated solid was stirred at room temperature for 12 hours, and worked up by filtering off with suction, washing with methanol and water and recrystallizing from toluene. Yield: 6.8 g (57%), melting point: 234°–236° C.

The method of Example 53 is also used to prepare the quinolinecarboxylic esters of Examples 54 and 55.

| Example No. | Quinoline derivative | Melting point [°C.] |
|---|---|---|
| 54 | (structure: 7-acetylamino quinoline-4-COOCH₃, 2-(3',4'-dimethoxyphenyl)) | 255–258 |

| Example No. | Quinoline derivative | Melting point [°C.] |
|---|---|---|
| 55 | (structure: 2-(3,4-dimethoxyphenyl)-6-acetamido-7-methoxy-quinoline-4-carboxylic acid methyl ester) | 248–249 |

EXAMPLE 56

The dye-forming component of Example 2 is dissolved in 0.5% strength in a diisopropylated naphthalene, and the solution is applied with a 6 μm doctor blade to a sheet of CF paper from Wiggins Teape. A yellow color develops. After exposure for one hour in the Suntest apparatus from Hanau, the ΔE value is determined by the CIELAB system. Prior art dye-forming components are treated in the same way.

|  | ΔE |
|---|---|
| Dye-forming component of Example 2 | 3 |
| Dye-forming component of EP-A-109930 Example 2 | 50 |
| Dye-forming component of GB-A-2136823 Example 14 | 14 |
| Dye-forming component of DE-A-2227597 Example 2 | 40 |

ΔE values of 1 are clearly visible.

We claim:

1. A quinoline-4-carboxylic acid derivative of the general formula I (structure I)

where one of
$R^1$, $R^2$ and $R^3$ is hydrogen while the other two are each independently of each other hydrogen, fluorine, chlorine, bromine, linear or branched $C_1$–$C_5$-alkyl, hydroxyl, $C_1$–$C_{10}$-alkoxy, which may be interrupted in the alkyl by 1 or 2 oxygen atoms, or is $$-N\begin{matrix}R^7\\R^8\end{matrix}$$

$R^7$ is hydrogen, methyl or ethyl and
$R^8$ is $C_1$–$C_4$-alkanoyl, benzoyl, p-chlorobenzoyl, $C_1$–$C_6$-alkyl, benzyl or p-chlorobenzyl, or
$R^1$ and $R^2$ together are a fused-on benzene ring,
$R^2$ and $R^3$ together are unsubstituted or $C_1$–$C_4$-alkyl-substituted methylenedioxy or ethylenedioxy, $R^4$ is hydroxyl, $C_1$–$C_{10}$-alkoxy, which may be interrupted by 1–4 oxygen atoms, or unsubstituted or chlorine-substituted phenyl-$C_1$–$C_2$-alkoxy,
$R^5$ is hydroxyl or $C_1$–$C_{10}$-alkoxy, although ortho-disposed $R^4$ and $R^5$ together may also be methylenedioxy or 1,2-ethylenedioxy,
$R^6$ is hydrogen, hydroxyl, methoxy, ethoxy, chlorine, fluorine or $C_1$–$C_4$-alkyl, and
X $C_1$–$C_{20}$-alkoxy, benzyloxy, p-chlorobenzyloxy, phenylethyloxy, cyclopentoxy, cyclohexoxy or $$-N\begin{matrix}R^9\\R^{10}\end{matrix}$$

where
$R^9$ is hydrogen, methyl or ethyl and
$R^{10}$ is hydrogen, $C_1$–$C_{20}$-alkyl, unsubstituted or chlorine- or methoxy- or methyl-monosubstituted or -disubstituted phenyl or a radical of the formula (structure II)

where
$R^1$ to $R^6$ are each as defined above,
Z is oxygen or >N—$R^9$ and
$R^{13}$ is linear or branched $C_2$–$C_{10}$-alkylene, which may be interrupted by up to 4 oxygen atoms, or is 1,2-, 1,3- or 1,4-xylylene.

2. A quinoline-4-carboxylic acid derivative as claimed in claim 1, wherein one of
$R^1$, $R^2$ and $R^3$ is hydrogen, fluorine, chlorine, bromine, linear or branched $C_1$–$C_5$-alkyl, hydroxyl or $C_1$–$C_{10}$-alkoxy, which may be interrupted in the alkyl by 1 or 2 oxygen atoms, and the other radicals are hydrogen.

3. A quinoline-4-carboxylic acid derivative as claimed in claim 1, wherein
$R^1$ is hydrogen and
$R^2$ and $R^3$ are each unsubstituted or methyl-substituted methylenedioxy or ethylenedioxy.

4. A quinoline-4-carboxylic acid derivative as claimed in claim 1 or 2, wherein
X is $C_1$–$C_{20}$-alkoxy, benzyloxy, phenylethyloxy, cyclopentoxy, cyclohexoxy or

where
- $R^9$ is hydrogen, methyl or ethyl and
- $R^{10}$ is $C_1$–$C_{20}$-alkyl, or unsubstituted or chlorine- or methoxy- or methyl-monosubstituted or -disubstituted phenyl.

5. A quinoline-4-carboxylic acid derivative as claimed in claim 1 of the formula

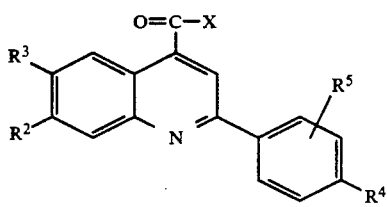

(III)

where $R^2$, $R^3$, $R^4$ and $R^5$ are each as defined in claim 1 and X is $C_1$–$C_{20}$alkoxy or

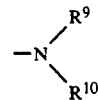

where
- $R^9$ is hydrogen, methyl or ethyl and
- $R^{10}$ is $C_1$–$C_{10}$-alkyl or phenyl.

6. A quinoline-4-carboxylic acid derivative as claimed in claim 5, wherein $R^2$ is hydrogen or $C_1$–$C_5$-alkoxy.

7. A quinoline-4-carboxylic acid derivative as claimed in claim 1, wherein said substituent X, as $C_1$–$C_{20}$-alkoxy, is methoxy, ethoxy, propoxy, isopropoxy, butoxy, isobutyoxy, sec-butoxy, t-butoxy, pentoxy, isoamyloxy, t-amyloxy, neopentyloxy, hexyloxy, 2-ethyhexyloxy, heptoxy, octyloxy, nonyloxy, decyloxy, dodecyloxy, cetyoxyl or octanedecyloxy.

8. A quinoline-4-carboxylic acid derivative as claimed in claim 1, wherein $R^{10}$, as $C_1$–$C_{20}$ alkyl, is methyl, ethyl, propyl, isopropyl, butyl, isobutyl, sec-butyl, t-butyl, hexyl, 2-ethylhexyl, octyl or decyl.

* * * * *